(12) United States Patent
Goren et al.

(10) Patent No.: US 6,340,483 B1
(45) Date of Patent: Jan. 22, 2002

(54) ANTIVIRAL COMPOSITION DERIVED FROM ALLIUM CEPA AND THERAPEUTIC USE THEREOF

(75) Inventors: Adolfo Goren, Cordoba (AR); Walter Franklin Goldman, Houston, TX (US); Zila Trainin, Rehovot (IL); Simon Raul Goldman, Cordoba (AR)

(73) Assignee: Diepon, S.A., Montevideo (UY)

( * ) Notice: Subject to any disclaimer, the term of this patent is extended or adjusted under 35 U.S.C. 154(b) by 0 days.

(21) Appl. No.: 09/631,284

(22) Filed: Aug. 3, 2000

(51) Int. Cl.$^7$ ................................................ A61K 35/78
(52) U.S. Cl. ........................................ 424/754; 514/707
(58) Field of Search .............................. 424/195.1, 754; 514/934, 707

(56) References Cited

FOREIGN PATENT DOCUMENTS

| EP | 0653206 A1 | * | 7/1993 |
| EP | 0745332 A1 | * | 12/1996 |

OTHER PUBLICATIONS

Van Damme et al., Plant Molecular Biology (1993) vol. 23, pp. 365–376.*

* cited by examiner

*Primary Examiner*—Jon P. Weber
*Assistant Examiner*—Harry J. Guttman
(74) *Attorney, Agent, or Firm*—Burns, Doane, Swecker & Mathis, L.L.P.

(57) ABSTRACT

Novel medicinal extracts derived from Allium species, preferably *Allium cepa* are provided. These extracts have broad medicinal properties, especially for treatment of AIDS and other viral infections.

7 Claims, No Drawings

ANTIVIRAL COMPOSITION DERIVED FROM ALLIUM CEPA AND THERAPEUTIC USE THEREOF

FIELD OF THE INVENTION

The invention relates to a novel plant extract and therapeutic use thereof. More particularly, the present invention relates to the use of a novel plant extract for treating AIDS and other viral infections.

BACKGROUND OF THE INVENTION

The use of plant derived compositions as therapeutic agents has been known for thousands of years. In particular, the Chinese are known for their herbal therapies. Recently, there has been a resurgence in the use of natural and plant-derived materials that supposedly possess therapeutic activity and promote general well being. For example, many persons now take St. John's Wort, purportedly to alleviate depression and promote general well being. Also, Ginkgo Biloba, purportedly to enhance memory, is widely used now. Further, SAMe, a yeast-derived material which purportedly is useful for treatment of osteoarthritis and alleviation of depression, is in wide use.

In particular, the use of materials derived from a plant of the Allium family, especially *Allivum sativum* ("garlic") has been reported in the literature. For example, several patents by Tatarintsev et al report the use of ajoene compound, derived from the garlic plant, for treating a variety of ailments including AIDS, inflammation, arthritis, transplant, infection, autoimmune diseases such as lupus, tuberculosis, tumors, and other relates diseases. (See U.S. Pat. Nos. 5,856,363; 5,863,955; 5,948,821; and 5,932,621.)

Also, Hibi, U.S. Pat. No. 5,612,077, describes an ajoene-containing extract from garlic for use in treating arteriosclerosis, tuberculosis, and bronchitis. Further, Tsuei, U.S. Pat. No. 4,795,636; Seebeck, U.S. Pat. No. 2,642,374; and Spinka et al, U.S. Pat. No. 2,618,561, describe garlic extracts as medicinal agents.

Further, the isolation of compounds from plant materials, including Allium that inhibit apoptosis has been reported. See especially, U.S. Pat. Nos. 5,567,425; 5,759,548; 4,986,985; 5,620,885; 5,624,672; 5,635,186; and 5,635,187, by Bathurst et al, all of which are incorporated by reference in their entirety herein.

The foregoing is only exemplary of plant-derived materials reported to possess medicinal properties. However, notwithstanding the large number of plant-derived materials reported to possess therapeutic properties, there still exists a need for novel plant extracts and therapeutic use thereof as such therapies may be safer and more cost effective than traditional medical treatments.

OBJECTS OF THE INVENTION

It is an object of the invention to provide a novel plant extract derived from a plant species of the family Alliaceae (also known as Lilliaceae or Amaryllidaceae), preferably of the genus Allium, with the proviso that said Allium is not garlic (*Allium sativum*), having medicinal properties.

It is a more specific object of the invention to provide novel plant extracts derived from an Allium species selected from the group consisting of *Allium cepa, Allium ampeloprasum* ("leek"), *Allium fistulosa* (Japanese bunching onion, scallion or Welsh onion), or *Allium schoenoprasum* ("chives") having medicinal properties.

It is an even more specific object of the invention to provide a novel plant extract derived from *Allium cepa*, preferably *Allium cepa* var. *Ancasti* or Southporth white glove (SWG) having medicinal properties.

It is a more specific object of the invention to provide a novel method of treating or preventing a retroviral infection such as HIV-1 or HIV-2 or AIDS by administering a plant extract derived from an Allium species other than *Allivum sativum*, preferably *Allium cepa, Allium fistulosa, Allium ampeloprasum* or *Allium schoenoprasum*, and most preferably *Allium cepa*.

It is a more specific object of the invention to treat wasting syndrome, especially associated with AIDS, and/or to lengthen the latency period of HIV infection, and/or to delay the latent phase of AIDS, and/or to ameliorate or eliminate the clinical symptoms associated with AIDS such as intestinal problems, diarrhea, neurological impairment and paresthesia by administering a medicinal extract derived from an Allium species other than *Allivum sativum*, preferably *Allium cepa, Allium fistulosa, Allium ampeloprasum* or *Allium schoenoprasum*, and more preferably *Allium cepa*.

It is another specific object of the invention to inhibit or treat microbial infection, e.g., fungal, yeast or Candidiasis infection in a subject in need of such inhibition or treatment, comprising administering a medicinal extract derived from an Allium species other than *A. sativum*, preferably *Allium cepa, Allium fistulosa, Allium ampeloprasum* or *Allium schoenoprasum* and most preferably *Allium cepa*.

It is another specific object of the invention to modulate the immune system of a subject in need of such treatment, by administering a medicinal extract derived from an Allium species other than *Allivum sativum*, preferably *Allium cepa*.

It is an object of the invention to provide a novel method of treating or preventing viral infection by administering a medicinal extract derived from an Allium species other than *Allivum sativum*.

It is a more specific object of the invention to provide a novel method of treating or preventing viral infection by administering a medicinal extract derived from an Allium species selected from the group consisting of *Allium cepa, Allium ampeloprasum, Allium fistulosa*, and *Allium schoenoprasum*.

It is an even more specific object of the invention to provide a novel method of treating or preventing viral infection by administering a medicinal extract derived from *Allium cepa*, preferably the variety Ancasti or Southporth white glove.

It is another object of the invention to immunostimulate the immune system of a subject in need of such treatment by administering a medicinal extract derived from an Allium species other than *sativum*, preferably *Allium cepa, Allium fistulosa, Allium schoenoprasum* or *Allium ampeloprasum* and more preferably *Allium cepa*.

It is another object of the invention to enhance T cell function and/or T cell proliferation, and/or T-cell differentiation, by administering a medicinal extract derived from an Allium species other than *Allivum sativum*, preferably *Allium cepa, Allium fistulosa, Allium schoenoprasum* or *Allium ampeloprasum*, most preferably *Allium cepa*.

It is another specific object of the invention to identify and isolate the active constituent or constituents comprised in the Allium extract disclosed herein having antimicrobial, antifungal, antiviral, immunomodulatory, T cell function or proliferation inducing, and/or immunostimulatory activity.

It is another specific object of the invention to promote weight gain in a subject in need of such treatment by administering an effective amount of a medicinal extract derived from an Allium selected from *Allium cepa, Allium fistulosa, Allium schoenoprasum* or *Allium ampeloprasum*, most preferably *Allium cepa*.

It is another object of the invention to treat animal microbial infections, especially viral infections such as distemper or parvovirus or bacterial infections such as psittacosis, by administering a medicinal extract derived from *Allium cepa*.

It is another object of the invention to provide a method for producing a medicinal extract from Allium species selected from *Allium cepa, Allium fistulosa, Allium schoenoprasum* or *Allium ampeloprasum*.

It is another object of the invention to provide a novel medicinal extract derived from *Allium cepa, Allium fistulosa, Allium schoenoprasum,* or *Allium ampeloprasum*, preferably orally administrable.

It is another specific object of the invention to provide a novel regimen for treating AIDS that includes a dietary regimen, no administration of conventional AIDS medications such as protease inhibitors, anti-retrovirals, or other chemotherapeutics causing multiple side effects (other than antibiotics) and administration of a medicament derived from a plant of the genus Allium, preferably *Allium cepa*.

DETAILED DESCRIPTION OF THE INVENTION

The present invention is based on the discovery that plants of the family Alliaceae, specifically those of the genus Allium, including *Allium cepa*, and related species such as *Allium fistulosa, Allium schoenoprasum,* and *Allium ampeloprasum*, can be used to obtain plant extracts having significant medicinal properties. In particular, it has been surprisingly discovered that extracts derived from Allium species, preferably *Allium cepa*, have wide ranging medicinal properties, including antiviral activity, antimicrobial activity (antifungal, antibacterial), immunomodulating activity, immunostimulating activity, T-cell function and/or T-cell proliferation and/or T-cell differentiation enhancing activity, and weight gain promoting activity.

This discovery is surprising in the fact that onions, while anecdotally reported to possess some medicinal properties, e.g., inhibition of thrombocyte aggregation and lipid and blood pressure lowering activity, have never been suggested to possess the wide ranging medicinal activities discovered by the present inventors, especially regarding AIDS.

Therefore, the subject invention provides novel medicinal extracts and methods of use thereof, wherein such medicinal extracts are derived from a plant of the family Alliaceae (also known as Liliaceae or Amaryllidaceae), preferably Allium but excluding *Allivum sativum*, and preferably *Allium cepa, Allium fistulosa, Allium schoenoprasum* or *Allium ampeloprasum*. Most preferably, the novel medicinal extracts of the present invention will be derived from onion (*Allium cepa L.*).

The onion, *Allium cepa L.* (2n=16 diploid), is a monocotyledon of the family Alliaceae which is by far the most economically important bulb vegetable. It is thought that the onion originated in Persia (Nonnecke,Ill., "Vegetable Production", Van Nostrand Reinhold, N.Y. (1989)) cultivated by the Egyptians, Greeks and Romans and brought to North America by the Spaniards. The onion has long been considered to possess medicinal value (Nonnecke (Id.)).

*Allium cepa* is divided into three main groups.

1. The common onion—bulbs are formed as single plants, and the inflorescence does not form bulbets (Nonnecke, (Id.)1989). The bulk of the onion cultivars belong to this group, which is the most important commercially (Nonnecke, (Id.)1989). It is propagated in the main from true seeds. Within this group exist extremes of bulb shapes (present-day cultivars include the Sweet Spanish, Bermuda, and globe onions), dry scale color (white, yellow, and red predominating), pungency (ranging from mild and sweet to pungent), and other characteristics (Nonnecke, (Id.)1989). When harvested early they produce spring or bunching onions (Lorenz, Onion, In "The Software Toolworks Multimedia Encyclopedia", Version 1.5, Grolier, Inc. (1992)). The onion plant is potentially a biennial, producing large bulbs the first year and seed the next (Lorenz, (Id.)1992). Plants may be grown from seed, as transplants of seedlings, or as small bulbs (sets) produced from thickly planted seed; when replanted, these bulbs reach maturity rapidly (Lorenz, (Id.)1992). Mature onions are usually dried before marketing (Lorenz, (Id.)1992).

2. The aggregatum group—characterized by many lateral bulbs or shoots, inflorescences lacking bulbets, sterile seed production, and propagation by vegetative means (Nonnecke, (Id.)1989). This group includes the potato onion or multiplier onion, ever-ready onions, and shallots (shallots are sometimes called scallions, a source of confusion because *A. fistulosum* is also called scallions) (Nonnecke, (Id.)1989).

3. The proliferous (proliferum) group—in this group, ground bulbs are sometimes poorly developed, the inflorescence bears bulbets, true seed is usually lacking, and therefore reproduction is by vegetative inflorescence and bulbets (Nonnecke, (Id.)1989). These are not commercially cultivated; they are used almost exclusively for home gardening (Nonnecke, (Id.)1989). The most common names for this group are tree onions, top-set onions, and Egyptian onions (Nonnecke, (Id.)1989).

The common onion (1. above), is a herbaceous biennial normally producing seed stems in the form of an umbel consisting of florets (Nonnecke, (Id.)1989). The swollen base of the stem forms a bulb made up of numerous fleshy leaves (Nonnecke, (Id.)1989). Short day length varieties are adapted for use in areas south of 30° N (Nonnecke, (Id.) 1989). Medium day length varieties are adapted to mild areas from 30° N to about 38° N, in areas where comparatively mild winters occur: south to central California, Georgia and mid-Atlantic states (Nonnecke, (Id.)1989). The long day onions are adapted for spring seeding or transplanting in sites north of 38° N (Nonnecke, (Id.)1989). The longer day length compensates for the shortness of the growing season by providing longer periods of photosynthetic activity (Nonnecke, (Id.)1989). It is absolutely critical to choose the appropriate cultivar for the appropriate environment; when short-day cultivars are grown in a long-day growing area or vice versa, the onion will not perform as expected (Nonnecke, (Id.)1989).

Onions for dehydration are white and have high soluble solids (Nonnecke, (Id.)1989). They are grown mostly in California where the long growing season permits the right balance of solids and pungency desired for the dehydrated product (Nonnecke, (Id.) 1989). The American market classifies onions according to maturation time (Nonnecke, (Id.) 1989). The Bermuda Granex, a grano type that is mild and flat top shaped, is an early-maturing onion with little or no storage life (Nonnecke, (Id.)1989). The late crop onions, mostly globe shaped with yellow, white or red scales are mild or pungent depending on cultivar and environment, and usually store well over long periods (Nonnecke, (Id.)1989). The bulk of the seed is produced in an environment conducive to good seed set, such as California (Nonnecke, (Id.) 1989).

In general, the medicament of the present invention which is derived from *Allium cepa, Allium fistulosa, Allium schoenoprasum* or *Allium ampeloprasum*, and preferably *Allium cepa*, more preferably type Ancasti and Southporth white glove, is produced by dehydration of an Allium plant material other than *Allium Sativum* by one or more heating steps, typically effected at about 80° C./110° C. or higher, i.e., after an initial washing procedure, removal of non-viable materials and removal of other impurities such as stones, wires, etc., and processing of the dehydrated material into fine particles or granules, i.e., roughly having the consistency of talcum powder or confectionary sugar, such that the average particle size ranges from about 1 to 1,400 microns and, more preferably, ranges from about <250 to about 850 microns. This granulation or particulation procedure can be effected or known industrial devices for effecting granulation, or in particular by use of high speed cutters such as those available from Moulinex or other suppliers. Such granulation will preferably be effected at low humidity, e.g., $\leq 5\%-7\%$ humidity, in order to prevent aggregation or clumping of particles or granules during processing. It is hypothesized by the present inventors that the particulate size of the subject medicament may enhance its medicament properties, perhaps because of increased surface area. Alternatively, it is speculated that particles of such size may facilitate absorption or uptake of the active constituent by specific cells, e.g., immune cells, and thereby potentiate its effect on the immune system.

Preferably, the utilized procedure for particulating the processed dehydrated Allium, preferably *Allium cepa*, material will result in most (greater than 95%) of the particles or granules in the resultant composition having an average size ranging from 1 to 1,400 microns, more preferably most of the particles will have an average particle size in the range of $\leq 10$ microns to about 850 microns, and most preferably most of the particles will have an average size within the range of 36 to 500 microns.

A preferred procedure for producing an Allium medicinal extract according to the invention comprises the following steps. This process is exemplary of the processes that can be used to produce the novel medicinal extract of the invention. Indeed, it is anticipated that the ordinary routineer will be able to modify this procedure without adverse effects, e.g., to reduce costs and enhance efficacy.

In the exemplary process, an Allium plant material, preferably *Allium cepa, Allium fistulosa, Allium ampeloprasum* or *Allium schoenoprasum*, preferably *Allium cepa*, including at least the bulb portion of the plant, is obtained. In a preferred embodiment, the selected *Allium cepa* material will comprise *Allium cepa* variety *ancasti* or Southporth white glove. However, this is not essential to the invention, and other *Allium cepa* varieties may alternatively be utilized. Preferably, the selected *Allium cepa* or above-identified Allium species will be grown in the absence of herbicides, insecticides and other agrochemicals such as organic fertilizers. However, this also is not essential to the invention.

This Allium plant material, which includes especially the bulb portion of the plant, may be stored prior to medicament preparation, preferably under cold conditions, typically about 10° C. at 70% humidity, or about 5–15° C. at 60–80% humidity. For example, the Allium plant material may be stored in wooden boxes (bines) for prolonged period, e.g., at least 30 days, and up to about 4 months. If stored for longer periods, the active constituents may lose their activity, e.g., because of natural decomposition of the onion over time.

Thereafter, the Allium plant material containing the bulb portion, optionally after it has been stored under appropriate conditions undergoes a quality evaluation. This material may also be classified based on size of plant materials.

Thereafter, the plant material is subjected to one or more washing procedures. Preferably, this washing will be effected under abrasive conditions on a conveyor belt which comprises use of an acidic aqueous washing solution, preferably a chlorinated aqueous solution. In a preferred embodiment, the washing solution will contain about 100 to 120 parts per million of chlorine. Preferably, no other chemical additives will be utilized during the washing procedure to eliminate fungus or bacteria. As noted, the washing is effected under abrasive conditions, i.e., the bulbs are also treated by abrasion, e.g., by a brushing procedure, at this time to remove the outer layers. Thereafter, one or more additional washing steps are then preferably effected, again using a chlorine-containing aqueous washing solution, preferably a cold chlorine-containing aqueous solution.

More specifically, the subject medicament is produced using an industrial process that complies with the F.D.A. regulations of the U.S.A. under the quality ISO 9000 norms. Preferably, the bulb recollection is industrial, not manual. After collection, the bulbs are preferably stored in wooden boxes of 1 m×1 m×1 m called bines. To maintain stability, such bulbs are stored in chambers at an average of 10° C. at 70% humidity (5–15° C. and 60–80% humidity.) The normal storage does range between 30 and 120 days.

This is followed by a quality evaluation (defects, solid material content, etc.). The optionally sorted bulbs are then sent to the elaboration plant.

The vegetal material is loaded in a large recipient or feeder to transport the material by a conveyor belt to start the first step in the process. In one embodiment the conveyor belt is made of a sequence of cylinders with brushes upon which the vegetal material rolls. Thereafter, "washing by abrasion" is effected with cold chlorinated water (e.g., about 7 to 15° C.). The chlorine concentration preferably ranges from 100 to 120 parts per million. No additive is used to eliminate fungus and bacteria. The bulbs are also brushed to eliminate the outer layers. This process of washing by abrasion is repeated a second time under identical conditions.

A belt is then used to transport the bulbs to the place where the material is sorted, e.g., manually, by discarding the non-viable one (e.g., green non-comestible or rotten material.) Thereafter, the material goes through a process of decantation eliminating foreign bodies such as stones, wires, etc. The bulbs are then cut into thin slices (e.g. 2–7 mm), preferably about 2–4 mm., e.g., by use of a cutting machine, to help the process of selection and dehydration. This is followed by the process of dehydration. For example, in one embodiment, the material is transported using another belt, and the transported material is preferably then heated, e.g. in an oven of dry continuous heat, and preferably first at 80–100° C. for 45 minutes, followed by 90–110° C. for another 45 minutes, and finally dehydration is completed at 80–100° C. for 30 minutes. This final material (called virgin) contain 5–7% humidity. However, it is anticipated that the heating process may be varied without adverse effects.

The virgin is kept in sealed bags at 20 to 25° C., preferably under dark conditions, until it will be needed. When needed for use, the "virgin" material is then processed with another machine that strips the outer layers and leaves the pulp by pneumatic separation. In this way, the slices obtained are of pulp material. This pulp is then chopped into flakes, which preferably are kept sealed at 18–25° C., away from sunlight.

After drying, the plant material, which consists of the pulp (and optionally outer layers) is then loaded into an industrial processing device, e.g., high speed cutters. Other option is the use of devices such as "Moulinex", or from other suppliers, that processes this material into fine particles or granules.

Preferably this granulation is effected at very low humidity, i.e., maximum of about 5.5% humidity to avoid clumping, in order to provide granulates having an average particle size ranging from about 1 to 1,400 microns, more preferably from about ≦36 microns to 850 microns. The dried particles will typically comprise at most 5.5% water, and preferably less. In an exemplary composition produced according to the invention from *Allium cepa*, about 42.9% of particles were smaller than 250 microns, 56.9% were less than 355 microns, 74.7% were less than 500 microns, and 21.7% were between 500–850 microns, with 22.1% ranging from 106–250 microns, 6.8% ranging from 75–106 microns, 10.8% ranging in size from 36–75 microns, and 3.2% being <36 microns. Thus, the significant majority of particles are less than 500 microns, with most ranging from <36 to 850 microns.

The dried particulate material may be immediately used as a medicament or it may be stored for a prolonged time prior to usage. This material preferably will be stored under cold (typically about 18 to 25° C.), dark conditions, for up to a year or even longer. This will prevent degradation of active constituents, e.g., by oxidation or sunlight.

It is believed that the subject treatment process which essentially comprises acidic washing steps, heated dehydration, and granulation into very fine particles having the consistency of a fine powder, e.g., on the order of talcum powder, results in an extract having a substantially unchanged chemical composition from the original Allium material, except for the removal of water, scent, and some other volatile acids.

However, the present inventors do not rule out the possibility that the washing, dehydration process and the heating steps used in the subject matter may be facilitating one or more reactions that result in the formation of one or more medicament compounds that are not endogenously present in Allium or which were present in lower concentrations, may provide for the release of larger amounts of active constituents. With respect thereto, the subject inventors are uncertain as to what are the exact active constituent or constituents that are contained in the subject medicament composition.

However, it has been reported that *Allium cepa* comprises the compounds listed below.

1-(F)-β-FRUCTOSYL-SUCROSE
1-(METILSULFINYL)-PROPYL-METHYL-DISULFIDE
1-METHYLDITHIO-PROPANE
1-METHYLTRITHIO-PROPANE
1-0-CAFFEOYL-β-D-GLUCOSE
1-0-FERULOYL-β-D-GLUCOSE
1-0-P-COUMAROYL-β-D-GLUCOSE
1-PROPYLTRITHIOPROPANE
2,3-DIMETHYL-(D,L)-BUTANE-CIS-1-CIS-DITHIAL-S,S'-DIOXIDE
2,3-DIMETHYL-5,6-DITHIA-BICYCLO-(2,2,1)-HEXANE-5-OXIDE
2,3-DIMETHYLTHIOPHENE
2,4-DIMETHYLTHIOPHENE
2,5-DIMETHYLTHIOPHENE
b 24-METHYLENE-CYCLOARTENOL
28-ISOFUCOSTEROL
2-METHYL-BUT-2-EN-1-AL
2-METHYL-BUTANAL
2-METHYL-BUTYR-2-ALDEHYDE
2-METHYL-PENT-2-EN-1-AL
2-METHYL-PENTANAL
3,4-DIMETHYL-2,5-DIOXO-2,5-DIHYDROTHIOPHENE
3,4-DIMETHYLTHIOPHENE
31-NORCYCLOARTENOL
31-NORLANOSTENOL
4-α-METHYL-ZIMOSTENOL
5-DEHYDRO-AVENASTEROL
5-HEXYL-CYCLOPENTA-1,3-DIONE
5-METHYL-2-n-HEXYL-2,3-DIHYDROFURAN-3-ONE
5-OCTYL-CYCLOPENTA-1,3-DIONE
6 (G)-β-FRUCTOSYL-SUCROSE
9,10,13-TRIHYDROXY-OCTADEC-11-ENOIC-ACID
9,12,13-TRIHYDROXY-OCTADEC-10-ENOIC-ACID
ABSCISSIC-ACID
ACETAL
ACETIC-ACID
ALANINE
ALLICIN
ALLIIN
ALLIOFUROSIDE-A
ALLIOSPIROSIDE-A
ALLIOSPIROSIDE-B
ALLIO SPIRO SIDE-C

ALLIOSPIROSIDE-D
ALLYL PROPYL SULFIDE
ALLYL PROPYL TRISULFIDE
ALLYL-METHYL-DISULFIDE
ALLYL-METHYL-SULFIDE
ALLYL-METHYL-TRISULFIDE
ALLYL-PROPENYL-DISULFIDE
ALLYL-PROPYL-DISULFIDE
ALLYLTHIOL
ALUMINUM
AMMONIA
ARABINOSE
ARACHIDIC-ACID
ARGININE
ARSENIC
ASCORBIC-ACID
ASH
ASPARAGINE
ASPARTIC-ACID
BARIUM
BENZYL ISOTHIOCIANATE
BORON
BRASSICASTEROL
BROMINE
CADMIUM
CAFFEIC-ACID
CALCIUM
CALCIUM-OXALATE
CAMPHESTEROL
CARBOHYDRATES
CATECHOL
CEPAENES
CEPOSIDE-D
CHOLEST-7-EN-3-β-OL
CHOLESTEROL
CHOLINE
CHROMIUM
CIS-1-(PROPENYL-DITHIO)-PROPANE
CIS-2,3-DIMETHYL-5,6-DITHIO-CYCLO(2,2,1) HEPTANE-5-OXIDE
CIS-3,5-DIETHYL-1,2,4TRITHIOLANE
CIS-PROPANETHIOL-S-OXIDE
CIS-PROPENYL-PROPYL-DISULFIDE
CIS-PROPENYL-PROPYL-TRISULFIDE
CITOSINE
CITRIC-ACID
CITRULINE
COBALT
COPPER
CYANIDIN-3-0-LAMINARIBIOSIDE
CYANIDIN-3-0-β-D-DIGLYCOSIDE
CYANIDIN-BIOSIDE
CYANIDIN-DIGLYCOSIDE
CYANIDIN-MONOGLYCOSIDE
CYCLOALLIIN
CYCLOARTENOL
CYCLOEUCALENOL
CYSTEINE
CYSTINE
DIALLYL-DISULFIDE
DIALLYL-SULFIDE
DIALLYL-TRISULFIDE
DIHYDROALLIIN
DIISOPROPYL-TRISULFIDE
DIMETHYL-DISULFIDE
DIMETHYL-FURANE
DIMETHYL-SULFIDE
DIMETHYL-TETRASULFIDE
DIMETHYL-TRISULFIDE
DIMETHYL-TRISULFIDE
DIPHENYLAMINE
DIPROPENYL-DISULFIDE
DIPROPENYL-SULFIDE
DIPROPYL-DISULFIDE
DIPROPYL-TRISULFIDE
D-MANNITOL
EICOSEN-1-OL
EO
ETHANOL
ETHANOLAMINE
FATS
FERULIC-ACID
FIBER
FLUORINE
FRUCTOSAN
FRUCTOSE
FUMARIC-ACID
GIBERELLIN-A-4
GLUCINE
GLUCOFRUCTAN
GLUCOSE
GLUTAMINE
GLUTAN
GLYCINE
GLYCOLIC-ACID
GRAMISTEROL
HEXADECEN-1-OL
HISTIDINE
HYDROGEN SULFUR
IRON
ISOLEUCINE
ISOPROPYL-PROPYL-DISULFIDE
ISOPROPYL-PROPYL-TRISULFIDE
KAEMPFEROL
KAEMPFEROL-3,4'-DI-0-β-D-GLUCOSIDE
KAEMPFEROL-4',7-DI-0-β-D-GLUCOSIDE
KAEMPFEROL-4'-O-β-D-GLUCOSIDE
LEAD
LEUCINE
LINOLEIC-ACID
LITHYUM
LOPHENOL
LYSINE

MAGNESIUM
MALIC-ACID
MANGANESE
MERCURY
METHANOL
METHANOTHIOL
METHIONINE
METHIONINE-METHYLSULFONIUM
METHIONINE-SULFONE
METHYL-ALLIIN
METHYL-CIS-PROPENYL-DISULFIDE
METHYL-DITHIOMETHANE
METHYL-METHANOTHIOSULFONIUM
METHYL-PROPENYL-SULFIDE
METHYL-PROPENYL-TRISULFIDE
METHYL-PROPYL-DISULFIDE
METHYL-PROPYL-TRISULFIDE
METHYL-TRANS-PROPENYL-DISULFIDE
MEVALONIC-ACID
MOLYBDENUM
MUFA
MYRISTIC-ACID
MYROSINASE
NIACIN
NICKEL
NITROGEN
NONADECANOIC-ACID
N-PROPYL-MERCAPTAN
OLEANOLIC-ACID
OLEIC-ACID
OXALIC-ACID
PAEONIDIN-GLYCOSIDE
PALMITIC-ACID
PANTOTHENIC-ACID
P-COUMARIC-ACID
PECTIN
PELARGONIDIN-MONOGLYCOSIDE
PENTOSAN
PEROXIDASE
PHENILALANINE
PBLOROGLUCINOL
PHLOROGLUCYOL-CARBOXYLIC-ACID
PHOSPHORUS
P-HYDROXYBENZOIC-ACID
PHYROCATECOL
PHYTOHORMONE
PHYTOSTEROLS
PIPECOLIC-ACID
POTASSIUM
PROLINE
PROPAN-1-OL
PROPANAL
PROPANALDEHYDE
PROPANE-1-THIOL
PROP-CIS-ENYL-PROPYL-DISULFIDE
PROP-CIS-ENYL-PROPYL-TRISULFIDE
PROPENE
PROPENYL-PROPYL-SULFIDE
PROP-TRANS-ENYL-PROPYL-DISULFIDE
PROP-TRANS-ENYL-PROPYL-TRISULFIDE
PROPYL-METHANOTHIOSULFONATE
PROPYL-PROPANOTHIOSULFONATE
PROSTAGLANDIN-A-1
PROTEIN
PROTOCATECHUIC-ACID
PUFA
PYRUVIC-ACID
QUERCETIN
QUERCETIN-3,4'-DI-0-β-D-GLUCOSIDE
QUERCETIN-3-0-β-D-GLUCOSIDE
QUERCETIN-4'-7-DI-0-P-D-GLUCOSIDE
QUERCETIN-4-0-β-D-GLUCOSIDE
QUINIC-ACID
RAFFINOSE
RHAMNOSE
RIBOFLAVIN
RIBOSE
RUBIDIUM
RUTIN
S-(2-CARBOXY-PROPYL)-GLUTATHIONE
S-(β-CARBOXYBETA-METHYL-ETHER-CISTEINE
S-ALLIL-CYSTEINE
SAPONIN
SELENIUM
SELENO-CYSTEINE
SELENO-METHIONINE
SELENO-METHYLSELENOCYSTEINE
SELENO-METHYL-SELENOMETHIONINE
SELENOSIDE
SERINE
SFA
SILICON
SILVER
SINAPIC-ACID
S-METHYL-CYSTEINE
S-METHYL-CYSTEINE-SULFOXIDE
SODIUM
SPIRAEOSIDE
S-PROP-1-ENYL-CYSTEINE-S-OXIDE
S-PROPYL-1-ENYL CYSTINESULFOXIDE
S-PROPYL-CYSTEINE-SULFOXIDE
STEARIC-ACID
STIGMAST-7-EN-3-β-OL
STIGMASTEROL
STRONTIUM
SUCCINIC-ACID
SUCROSE
SULFUR
TARTARIC-ACID
THIAMIN
THIOPROPANAL-S-OXIDE
THIOPROPIONAL-S-OXIDE

TITANIUM
TRANS-1-(PROPENYL-DITHIO)-PROPANE
TRANS-2,3-DIMETHYL-5,6-DITHIA-CYCLO-(2,2,1)-HEPTANE-5-OXIDE
TRANS-3,5-DIETHYL-1,2,4-TRITHIOLANE
TRANS-PROPENYL-PROPYL-DISULFIDE
TRANS-PROPENYL-PROPYL-TRISULFIDE
TRANS-S-(1-PROPENYL)-CYSTEINE-SULFOXIDE
TREONINE
TREDECAN-2-ONA
TRIGONELLINE
TRYPTOPHAN
TSEPOSIDES
TULIPOSIDE-A
TULIPOSIDE-B
TYROSINE
VALINE
VANILLIC-ACID
VIT-B-6
WATER
XYLITOL
XYLOSE
ZINC
ZIRCONIUM
α-AMYRIN
α-SITOSTEROL
α-TOCOPHEROL
β-ALALNINE
β-CAROTENE
β-SITOSTEROL
β-TOCOPHEROL
γ-ABULINE
γ-AMINOBUTIRIC-ACID
γ-GLUTAMYL-LEUCINE
γ-GLUTAMYL-METHIONINE
γ-GLUTAMYL-PHENYLALANINE
γ-GLUTAMYL-PHENYLALANINE-ETHYL-ESTER
γ-GLUTAMYL-S-METHYL-CYSTEINE
γ-L-GLUTAMYL-ARGININE
γ-L-GLUTAMYL-CYSTEINE
γ-L-GLUTAMYL-ISOLEUCINE
γ-L-GLUTAMYL-S-(1-PROPENYL)L-CYSTEINE-SULFOXIDE
γ-L-GLUTAMYL-S(2-CARBOXY-N-PROPYL)L-CISTEINE
γ-L-GLUTAMYL-S-(2-CARBOXY-β-METHYL-ETHYL)-CYSTEINYL-GLY
γ-L-GLUTAMYL-S-(2-CARBOXY-β-METHYL-ETHYL)-CYSTEINYL-GLY
γ-L-GLUTAMYL-VALINE
CYANIDIN-3-MALONYLGLUCOSIDE
CYANIDIN-3-MANOLYLAMINARIBIOSIDE
PEONIDIN-3-GLUCOSIDE
PEONIDIN-3-MALONYLGLUCOSIDE
PHOSPHATASE
PROPILENSULFIDE
QUERCETIN-3,4'-O-β-DIGLUCOPYRANOSIDE
QUERCETIN-3,7,4'-O-β-GLUCOPYRANOSIDE
QUERCETIN-4'-O-β-GLUCOPYRANOSIDE
TAXIFOLIN-4'-O-b-GLUCOPYRANOSIDE
β-FRUCTOFURANOSIDASE
γ-GLUTAMYLTRANSPEPTIDASE

Of the above materials, those that are especially hypothesized to be responsible for the medicinal and immune regulating activity of the subject Allium extract are set forth below.

1-O-CAFFEOYL-b-D-GLUCOSE
1-O-P-COUMAROYL-b-D-GLUCOSE
ALLICIN
ALLIIN
ALLIOFURÓSIDE-A
ALLIOSPIRÓSIDE-A
ALLIOSPIRÓSIDE-B
ALLIOSPIRÓSIDE-C
ALLIOSPIRÓSIDE-D
ALLYL PROPYL SULFIDE
ALLYL PROPYL TRISULFIDE
ALLYL-METHYL-DISULFIDE
ALLYL-METHYL-SULFIDE
ALLYL-METHYL-TRISULFIDE
ALLYL-PROPENYL-DISULFIDE
ALLYL-PROPYL-DISULFIDE
CAFFÉIC-ACID
CAMPHESTEROL
CATECHOL
CHOLINE
CIS-PROPENYL-PROPYL-DISULFIDE
CIS-PROPENYL-PROPYL-TRISULFIDE
CYANIDIN-3-O-LAMINARIBIÓSIDE
CYANEDIN-3-O-b-D-DIGLYCÓSIDE
CYANIDIN-BIÓSIDE
CYANIDIN-DIGLYCÓSIDE
CYANIDIN-MONOGLYCÓSIDE
CYCLOALLIIN
DIALLYL-DISULFIDE
DIALLYL-SULFIDE
DIALLYL-TRISULFIDE
DIHYDROALLIIN
DIISOPROPYL-TRISULFIDE
DIMETHYL-DISULFIDE
DIMETHYL-SULFIDE
DIMETHYL-TETRASULFIDE
DIMETHYL-TRISULFIDE
DIPROPENYL-DISULFIDE
DIPROPENYL-SULFIDE
DIEPROPYL-DISULFIDE
DIPROPYL-TRISULFIDE
HYDRÓGEN SULFUR
ISOPROPYL-PROPYL-DISULFIDE
ISOPROPYL-PROPYL-TRISULFIDE
KAEMPFEROL-3,4'-DI-O-b-D-GLUCOSIDE
KAEMPFEROL-4',7-DI-O-b-D-GLUCOSIDE

KAEMPFEROL-4'-O-b-D-GLUCOSIDE
LYSINE
METHIONINE-METHYLSULFONIUM
METHIONINE-SULFONE
METHYL-ALLIIN
METHYL-CIS-PROPENYL-DISULFID
METHYL-METHANOTHIOSULFONIUM
METHYL-PROPENYL-SULFIDE
METHYL-PROPENYL-TRISULFIDE
METHYL-PROPYL-DISULFUIDE
METHYL-PROPYL-TRISULFIDE
METHYL-TRANS-PROPENYL-DISULFIDE
MYRÍSTIC-ACID
MYROSINASE
OLEANÓLIC-ACID
PAEONIDIN-GLYCOSIDE
PALMÍITIC-ACID
P-COUMÁRIC-ACID
PELARGONIDIN-MONOGLYCOSIDE
PROP-CIS-ENYL-PROPYL-DISULFIDE
PROP-CIS-ENYL-PROPYL-TRISULFIDE
PROPENYL-PROPYL-SULFIDE
PROP-TRANS-ENYL-PROPYL-DISULFIDE
PROP-TRANS-ENYL-PROPYL-TRISULFIDE
PROPYL-METHANOTHIOSULFONATE
PROPYL-PROPANOTHIOSULFONATE
PROSTAGLANDIN-A-1
QUERCETIN
QUERCETIN-3,4'-DI-O-b-D-GLUCÓSIDE
QUERCETIN-3-O-b-D-GLUCÓSIDE
QUERCETIN-4',7-DI-O-b-D-GLUCÓSIDE
QUERCETIN-4-O-b-D-GLUCÓSIDE
RUTIN
S-ALLIL-CYSTEINE
SAPONIN
SELENIUM
SELENO-CYSTEINE
SELENO-METHIONINE
SELENO-METHYLSELENOCYSTEINE
SELENO-METHYL-SELENOMETHIONINE
SELENÓSEDE
S-METHYL-CYSTEiNE-SULFÓXIDE
S-PROPYL ENYL-1-ENYL CYSTEINESULFÓXIDE
S-PROPYL-CYSTEINE-SULFÓXIDE
SULFUR
TRANS-PROPENYL-PROPYL-DISULFIDE
TRANS-PROPENYL-PROPYL-TRISULFIDE
TRANS-S-(1-PROPENYL)-CYSTEINE-SULFÓXIDE
a-AMYRIN
a-SITOSTEROL
b-SITOSTEROL
g-GLUTAMYL-LEUCINE
g-GLUTAMYL-METHIONINE
g-GLUTAMYL-PHENYLALANINE
g-GLUTAMYL-PHENYLALANINE-ETHYL-ESTER
g-GLUTAMYL-S-METHYL-CYSTEINE
g-L-GLUTAMYL-ARGININE
g-L-GLUTAMYL-CYSTEINE
g-L-GLUTAMYL-ISOLEUCINE
g-L-GLUTAMYL-S-(1-PROPENYL)L-CYSTEINE-SULFÓXIDE
g-L-GLUTAMYL-S(2-CARBOXY-N-PROPYL)1-CISTEINE
g-1,GLUTAMYL-S-(2-CARBOXY-b-METHYL-ETHYL)-CYSTEINYL-GLY
g-L-GLUTAMYL-VALINE
CYANIDIN-3-MALONYLGLUCÓSIDE
CYANIDIN-3-MANOLYLAMINARIBIOSIDE
QUERCETIN-3,4'-O-b-DIGLUCOPYRANOSIDE
QUERCETIN-3,7,4'-O-b-GLUCOPYRANOSIDE
QUERCETIN-4'-O-b-GLUCOPYRANOSIDE

Of these compounds, the following are believed to be the most likely candidates to be separately or jointly responsible for the medicinal properties of the subject Allium extracts.

1-O-CAFFEOYL-b-D-GLUCOSE
ALLICIN
ALLIIN
ALLYL PROPYL SULFIDE
ALLYL PROPYL TRISULFIDE
ALLYL-METHYL-DISULFIDE
ALLYL-METHYL-SULFIDE
ALLYL-METRYL-TRISULFIDE
ALLYL-PROPENYL-DISULFIDE
ALLYL-PROPYL-DISULFIDE
CAFFÉIC-ACID
CATECHOL
CHOLINE
DIHYDROALLIN
KAEMPFEROL-3,4'-DI-O-b-D-GLUCOSIDE
KAEMPFEROL-4',7-DI-O-b-D-GLUCOSIDE
KAEMPFEROL-4'-O-b-D-GLUCOSIDE
LYSINE
METHYL-METHANOTHIOSULFONIUM
OLEANÓLIC-ACID
PALMÍTIC-ACID
P-COUMÁRIC-ACID
PROPYL-METHANOTHIOSULFONATE
PROPYL-PROPANOTHIOSULFONATE
QUERCETIN
QUERCETIN-3,4'-Di-O-b-D-GLUCÓSIDE
QUERCETIN-3-O-b-D-GLUCÓSIDE
QUERCETIN-4',7-DI-O-b-D-GLUCÓSIDE
QUERCETIN-4-O-b-D-GLUCOSIDE
RUTIN
SAPONIN
SELENIUM
a-AMYRIN
a-SITOSTEROL
b-SITOSTEROL
CYANIDIN-3-MALONYLGLUCÓSIDE
CYANIDIN-3-MANOLYLAMINARIBIOSIDE

QUERCETIN-3,4'-O-b-DIGLUCOPYRANOSIDE
QUERCETIN-3,7,4'-O-b-GLUCOPYRANOSIDE
QUERCETIN-4'-O-b-GLUCOPYRANOSIDE

However, Applicants do not want to be bound by such hypotheses. In fact, it may be that the medicinal properties of the subject Allium extracts may involve different constituents, or may require a particular distribution of constituents that are selectively obtained by the aforedescribed processing procedure. Moreover, as discussed previously, the particulate size or other morphological properties of the material may also be significant to medicament activity.

The particles obtained by the described procedure may be administered by systemic or non-systemic means. Typically, the particles (in the form of a powder) will be placed in capsules that either dissolve in the stomach or intestine, or both, or will be used to make tablets, suppositories, sachets, or will liquid administrable forms, e.g., elixirs, syrups, or suspensions. Alternatively, these powders can be used to produce an injectable composition, e.g., by addition to a pharmaceutically acceptable excipient such as buffered saline. Of these modes of administration, oral administration is preferred. For example, in a preferred embodiment, capsules containing the powder according to the invention may be ingested with an ingestible fluid, e.g., juice, water, or milk. Still alternatively, the powders will be added to a food, e.g. solid or liquid that camouflages the taste of the particles, especially if the user does not like the taste of onion.

Methods for producing orally administrable materials having desired properties, e.g., sustained or rapid release, enteric-coated forms, are well known and are described in *Remington's Pharmaceutical Sciences*, Mack Publishers (incorporated by reference herein.)

In producing capsules, the subject Allium powder may be combined with other materials, if desired, e.g, sugars such as lactose, sucrose, mannitol, starches, cellulose derivatives, magnesium stearate or stearic acid. Also, materials that enhance aesthetic properties of the material may be added, e.g., colorants and flavoring materials. Additives which can be utilized in capsule formulations are well known to those skilled in the art.

If the subject powders are utilized to make tablets, conventional tableting procedures can be used which typically comprise processing the materials by compression to produce a tablet. Materials which facilitate tablet formation can be utilized, e.g., binders and bulking agents or other additives, including by way of example gums, waxes, insoluble polymers, polyvinyl alcohol, polyethylene glycol, sucrose, lactose, acacin, tragacanth, and polyvinyl pyrrolidine. Also, additives may be utilized which enhance taste and appearance, e.g., flavoring or coloring agents.

In a preferred embodiment, the tablets are coated such that they are selectively released in the stomach or intestine. With respect thereto, coatings which are acid-stable and allow for drug release in the intestine (referred to generally as enteric coatings) are well known. Examples include shellac and derivatives thereof, cellulose acetate phthalate, hydroxypropyl/methylcellulose phthalate, ethyl cellulose. Such enteric coating and methods for application thereof are discussed in detail in *Remington's Pharmaceutical Sciences*, (Id.) Also, U.S. Pat. Nos. 4,017,647 and 4,287,221 are exemplary of enteric coated drug formulations. The enteric coated form should enhance the antimicrobial properties of the powder.

Alternatively, and preferably in the case of subjects that find solid dosage formulations difficult to take (which may be a significant concern in AIDS patients who at latter stages may have swallowing problems), the subject materials may be produced in the form of liquid elixirs, or other liquids. This can be effected by combining the subject Allium powder with fruit or other vegetable juices, sugars, flavoring materials, or other materials having known application in liquid drug formulations. This is further advantageous for subjects that find the taste of the subject material disagreeable. Still alternatively, the subject material may be combined with solid foods, e.g., in order to camouflage the taste, if desired.

As noted, a less preferred means of administration will comprise injectable formulations. In this embodiment, the powder will be combined with an injectable liquid, e.g., buffered saline, and injected by known routes, e.g., intravenous, intramuscular, intradermal, or subcutaneous routes of administration. For example, a subject with an AIDS-associated lesion may be injected at the site of lesion to elicit an immune modulating or T-cell response.

Other modes of administration include topical, inhalatory, intranasal, sustained release implants, and rectal or vaginal suppositories.

The amount ofparticles which are administered, e.g., orally, injection, suppository, intranasal, will typically range from about 5–50 grams per day, and more preferably about 9 to 13 grams per day. A particular advantage of the medicament of the present invention is that there are no known side effects. Consequently, there are no real upper dosage ranges.

A general description of properties of the subject material is summarized below.

1. Description of the Medicinal Allium Product of the Invention

Properties of the medicinal product of the invention were evaluated by placing 10 grams of this material in 500 ml of boiled water and heated for 10 minutes. The rehydrated vegetable exhibited the following characteristics:

| Look & Color | Flavor | Aroma |
| --- | --- | --- |
| White flakes with some green particles | Characteristic | Characteristic |

2. Granulometric

| | | |
| --- | --- | --- |
| Retained on sieve | USA 3/8 (9.5 mm) | 5% max |
| Retained on sieve | USA 8 (2.36 mm) | 90% min |
| Through sieve | USA 8 | 5% max |

3. Humidity

Max 5.5%

4. Microbiological Analysis

| Total Aerobic Mesophiles | 300,000 | ufc/g | Maximum |
| Total Coliforms | 1,000 | NMP/g | Maximum |
| E. coli | Negative | | |
| Reduce sulphite Clostridium | 10 | ufc/g | Maximum |
| Yeast and Molds | 1,000 | ufc/g | Maximum |

As noted above, the subject materials can be stored for prolonged periods prior to usage, preferably by storing in a dry, ambient temperature conditions, i.e., about 18–25° C., preferably in the dark to avoid oxidation. Preferably, the material will be stored in a sealed plastic bag or other container to maintain low humidity and avoid microbial or other contamination.

As discussed previously, the subject medicament has a number of different properties that render it well suited for use as a therapeutic. For example, it has been found that the subject Allium derived medicament has broad antiviral activity. The subject extract may be used to treat or prevent a variety of different viral infections, both human and animal viruses. Examples thereof include retroviral infections such as AIDS, herpes (genital, rectal, oral), distemper, papillomavirus, flu associated influenza viruses, parvoviruses, rhabdoviruses, Epstein Barr virus, CMV, hepatitis virus, RSV, rhinoviruses, and foot and mouth disease virus.

In the preferred embodiment, the subject Allium derived medicament will be used for the treatment of AIDS. Entirely unexpectedly, it has been found that administration of the subject medicament to patients with AIDS results in disappearance of elimination of the clinical symptoms associated therewith, such as wasting syndrome, paresthesia intestinal colic, diarrhea, polyadenopathy, and HIV related infections. To date, these results have been observed in eight different patients having an age ranging from 28 to 38, many of which were in the latter terminal ("C-stage") of AIDS. These clinical results are summarized in the example infra.

In effecting the HIV treatment protocol of the invention, patients with AIDS will be withdrawn from anti-AIDS conventional medications such as protease inhibitors, anti-retrovirals, cytotoxic drugs, steroids, chemotherapies, and preferably will be placed on a restricted diet developed by the inventors. The use of tobacco and other smoking products or narcotics is also forbidden.

This diet preferably comprises ingestion of only natural products (without preservatives, and chemical additives) such as vegetables, fruits, fish, meat in small quantities, no fried foods, no alcoholic beverages, no caffeinated beverages such as coffee, tea, and no sweetened drinks such as sodas. The use of tobacco and other smoking products, or narcotics, is also forbidden. If intestinal irregularities result because of ingestion of large amounts of vegetables and fruit, this preferably will be treated by ingestion of rice, white bread, cheese, apples or lemon. However, if necessary an anti-diarrheic medicine may be administered. Moreover, if significant weight loss results, then unfried potatoes, preferably about 250 grams twice a day may be ingested.

The subject AIDS therapy will comprise administration, preferably about 9–13 g/day of the subject medicament. Preferably, his will be effected orally, e.g., in capsule form by mixing in a suitable beverage or with food. However, other known modes of administration can be used. This treatment should be continued for the life of the patient. A maintenance dose is established once the patient is free of symptoms. This maintenance dosage typically will range from about 5–7 g/day. In fact, it has been observed for some patients who have stopped this treatment, that AIDS symptoms have relapsed. However, when these patients resumed the subject treatment, remission (absence of clinical symptoms) again resulted. Ideally, the treated patients will also undergo an exercise regimen/regime to help enhance overall wellness.

Also, the subject medicament may be used to treat other conditions. In particular, the subject medicament may be used to modulate the immune system, stimulate the immune system, and/or enhance T cell function and/or proliferation in subjects in need of such treatment. Examples where such treatment will be of therapeutic benefit include boosting the immune systems of aged or immunosuppressed persons, persons with cancer, and persons with infection. In particular, the subject medicament has application in treatment and/or prevention of microbial infection, e.g., by fungi.

Still further, the subject medicament may be used to induce weight gain in persons in need of such treatment, e.g., those suffering from anorexia.

These treatments will be effected substantially the same as AIDS treatment, i.e., an effective amount of the subject *Allium cepa* material will be administered, preferably by oral administration, typically a daily dosage of about 9–13 g/day or more.

Also, the subject medicament may be used to treat infections, e.g., viral or bacterial infections, in animals such as dogs, cats, and birds. In fact, the means by which the subject medicament was initially shown to be effective involved treatment of a dog with parvovirus infection. As with AIDS treatment, this treatment has been observed to totally eradicate the clinical symptoms of the disease in the treated animal. Other animal diseases which have been treated include distemper, and psittacosis.

Still other diseases and conditions treatable with the subject Allium extract include candidiasis, e.g. pneumonia, caused by Pneumocistis carinii, urinary infection, and mycosis.

EXAMPLE

*Allium cepa* extracts produced according to the invention were orally administered to eight persons that are HIV$^+$, most of them with full blown AIDS. In fact, some of these persons were close to death when treatment initiated. Treatment comprised stopping conventional treatment, starting of the dietary regimen according to the invention, and oral ingestion of about 9 to 13 g/day of the subject Allium extract daily. As can be seen from the results in the Table below, dramatic results were achieved, i.e., all of these eight persons had a total remission of clinical symptoms associated with AIDS and were able to resume a normal life style after treatment.

| CLINICAL CHARACTERISTICS OF PATIENTS WITH HIV INFECTION TREATED WITH IMMUNO-PLUS AND DIETARY REGIMEN |||||||||||
| --- | --- | --- | --- | --- | --- | --- | --- | --- | --- | --- |
| PATIENT No. | 103* | 105 | 101 | 109 | 108 | 106* | 107* | 102* |
| AGE | 38 | 28 | 32 | 34 | 29 | 31 | 30 | 30 |
| SEX | M | M | M | M | M | M | M | M |
| DATE HIV DIAGNOSIS | 1991 | 1994 | 1994 | 1993 | 1993 | 1996 | 1994 | 1997 |
| CDC CATEGORY | C.2 | C.2 | C.2 | B.1 | A.1 | C.1 | B.1 | C.3 |
| STARTING DATE | 9-1-97 | 6-26-97 | 6-24-97 | 6-4-93 | 10-6-93 | 3-25-96 | 1-28-94 | 11-10-97 |
| PREVIOUS MEDICATION | ANTIBIOTICS (BACTRIM) | ANTIBIOTICS, ANTIMICOTICS, ANTACIDS | NO | NO | NO | NO | ANTIBIOTICS (BACTRIM) | SUSPENDED ANTIRETROVIRALS 8 DAYS AGO |
| ADENOPATHY | INGUINAL BILATERAL LEFT ARMPIT | NO | OCCIPITAL, CERVICAL | POLYADE-NOPATHY | NO | ADENOPATHY, CERVICAL, ARMPIT | CERVICAL-ARMPIT BILATERAL | POLYADENOPATHY |
| CONSTITUTIONAL SYNDROME | <WEIGHT, INTESTINAL DIARRHEA, 38° C. PERSISTENT | 39° C. | <WEIGHT, <7 KG 90 DAYS, INTERMIT. UP TO 38° C. | <WEIGHT FEVER | NO | <4 KG-6 MO. INTERMIT. DIARRHEA, FEVER | <4 KG-CONT. DIARRHEA, FEVER | <18 KG-6 MONTHS CONT. DIARRHEA, FEVER 38° C. |
| HISTORY OF HIV RELATED INFECTIONS | ORAL/RECTAL HERPES, OROFARINGEAL MICOSIS, PNEUMONIA | ORAL HERPES, ORAL MICOSIS, PNEUMONIAS | ORAL HERPES, PNEUMONIA | NO | NO | PNEUMONIAS | PNEUMONIAS | RECTAL HERPES, SIGMOIDITS, PNEUMONIAS, URINARY INFECTIONS |
| GASTRO-INTESTINAL SYMPTOMS | EPIGASTRALGIA, ANOREXIA, DIARRHEA, INTESTINAL COLICS | NAUSEA, ANOREXIA, INTESTINAL COLICS | INTERMIT. DIARRHEA, INTESTINAL COLICS | NO | NO | ANOREXIA | ANOREXIA | INTESTINAL COLICS, INTESTINAL PERFORATION AND SURGERY ON 10-97 |
| OTHER CLINICAL ASPECTS | PARESTHESIAS OF LOWER LIMBS, DEPRESSION, RIGHT ORCHITIS | SEVERE SHORTNESS OF BREATH, OXYGEN THERAPY, RESERVED PROGNOSIS | DEPRESSION, GENERAL DISCOMFORT, ANXIETY | DEPRESSION, SUBMAXILLARY ABSCESS | NO | GASTRITIS, ANOREXIA | TREATED IN BUENOS AIRES FOR PNEUMONIAS | OPENED INFECTED SURGERY WOUND, EMACIATION, DYSPNEA III–IV, TERMINAL PATIENT |
| EVOLUTION JAN–FEB '98 | GAINED 4 KG, NO INFECTIOUS SYMPTOMATOLOGY, GOOD GENERAL CONDITION | >WEIGHT, PHYSICAL EXAMINATION NORMAL | PHYSICAL EXAMINATION NORMAL | PHYSICAL EXAMINATION NORMAL | PHYSICAL EXAMINATION NORMAL | PHYSICAL EXAMINATION NORMAL | PHYSICAL EXAMINATION NORMAL | >14 KG TO DATE, PALENESS, WEAKNESS, GOOD PROGRESS |
| EVOLUTION DECEMBER '99 | ALL PATIENTS ARE CURRENTLY IN GOOD CONDITION, PHYSICAL EXAM NORMAL(**) |||||||||

PNEUMONIAS: 80% PNEUMONIAS WITH PNEUMOCISTIS CARINII (PCP)  20% PNEUMONIAS W/COMMON GERMS (COCOS)
*RECEIVED ANTI-RETROVIRALS UNTIL STARTING WITH I+ (*Allium cepa* extract according to the invention)
**PHYSICAL EXAMINATION NORMAL
VITAL SIGNS WITHIN NORMAL LIMITS (BP, PULSE, TEMPERATURE IN DEGREES CELSIUS AND RESPIRATORY RATE)
NO WEIGHT LOSS
NO ADENOPATHIES
NO DIARRHEA
NO AIDS RELATED INFECTIONS
RESPIRATORY, CARDIO-VASCULAR, ABDOMINAL, GENITO-URINARY, RECTAL AND NEUROLOGICAL EXAMS, ALL NORMAL

What is claimed is:

1. A method for treating HIV-positive or AIDS patients comprising orally administering an amount of a dehydrated particulate *Allium cepa* plant material that is processed to provide particles wherein the majority have an average particle size ranging from about 36 to 500 microns, and wherein said dehydrated, particulate plant material is orally administered in an amount to reduce at least one of the clinical symptoms associated with HIV positive or AIDS patients, and further wherein dehydration is effected by heating;

wherein said clinical symptoms are selected from the group consisting of paresthesia, wasting syndrome, intestinal colic, diarrhea and polyadenopathy.

2. The method of claim 1 wherein said plant material is administered daily.

3. The method of claim 2 wherein said daily administration comprises about 9 g to 50 g of said dried, particulate plant material.

4. The method of claim 2 wherein said HIV patients are not treated with any other antiretrovirals or protease inhibitors.

5. The method of claim 1 wherein said AIDS patients are in the advanced stage of the disease.

6. The method of claim 2, wherein said daily administration comprises about 9 g to 13 g of said dried, particulate plant material.

7. The method of claim 1 wherein heating is effected at 80–110° C.

* * * * *